United States Patent [19]

Saitoh et al.

[11] Patent Number: 4,935,241
[45] Date of Patent: Jun. 19, 1990

[54] PHARMACEUTICAL PREPARATION FOR TINEA PEDIS

[75] Inventors: Izumi Saitoh, Hyogo; Kaori Ikeda, Osaka; Shigeru Kido, Osaka; Yoshio Doi, Osaka; Shohei Egawa, Hyogo, all of Japan

[73] Assignee: Shionogi & Co., Ltd., Osaka, Japan

[21] Appl. No.: 266,894

[22] Filed: Nov. 3, 1988

[30] Foreign Application Priority Data

Dec. 8, 1987 [JP] Japan ................... 62-310479

[51] Int. Cl.$^5$ .............................. A61K 31/78
[52] U.S. Cl. ...................... 424/81; 514/399; 514/858; 514/964
[58] Field of Search ............ 514/947, 969, 399; 424/81

[56] References Cited

U.S. PATENT DOCUMENTS 4,619,826 10/1986 Lay et al. ..................... 424/78
4,803,066 2/1989 Edwards ........................ 424/132

OTHER PUBLICATIONS

USAN and USP Dictionary of Drug Names, p. 153 (1989).
Chemical Abstracts 104: 10582w (1986).

Primary Examiner—Leonard Schenkman
Attorney, Agent, or Firm—Wenderoth, Lind & Ponack

[57] ABSTRACT

A pharmaceutical preparation for the treatment of tinea pedis, containing as basic components about 0.1% to about 2.5% of croconazole hydrochloride and about 1%–15% of an ethyl acrylate-methyl methacrylate copolymer in an aqueous alcohol, and if necessary, about 0.1% to about 2.5% of a thickening agent and/or a plasticizer.

5 Claims, 1 Drawing Sheet

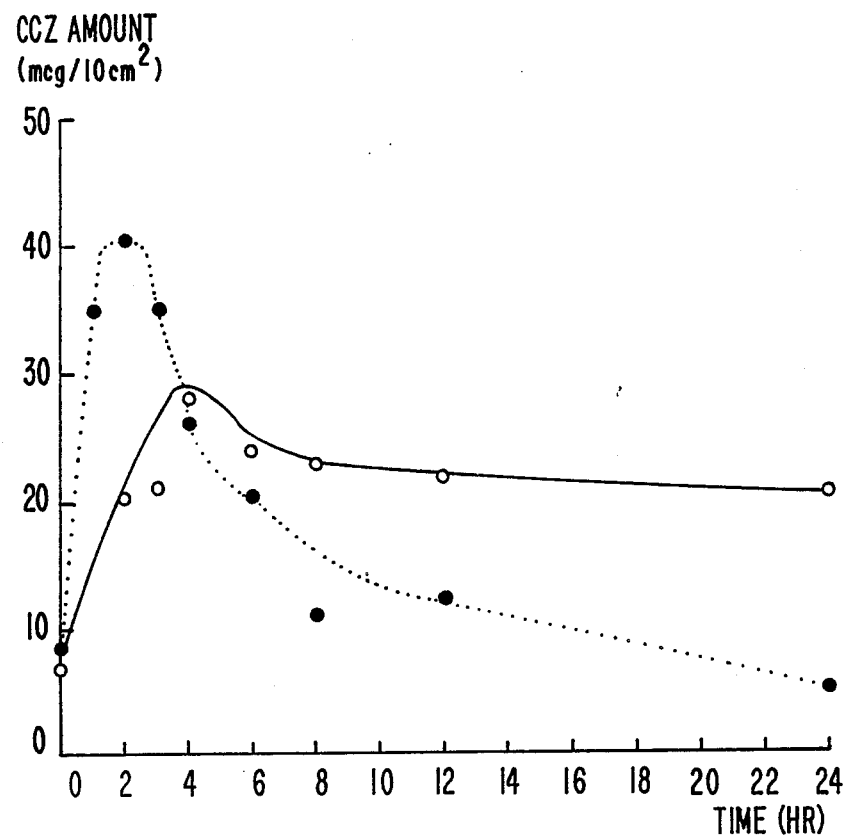

PHARMACEUTICAL PREPARATION FOR TINEA PEDIS

BACKGROUND OF THE INVENTION

1. Field of the Invention

The present invention relates to external preparations of croconazole hydrochloride (hereinafter abbreviated as CCZ) known as an antifungal agent.

2. Prior Art

CCZ is a potent antifungal agent which has been developed and marketed as cream- or gel-type preparations under the trade name of Pilzcin ® by Shionogi & Co., Ltd, and is enjoying wide popularity.

However, in many cases, mycosis as represented by athlete's foot primarily occurs at moist parts of the body. So, when an ointment or a gel preparation is applied to the affected part, it makes the affected part even more moist, thereby giving a strange feeling or staining of clothing. These are shortcomings in using ointments or gel preparations. A tincture has such shortcomings as to take a longer time to dry on the application parts.

To solve these shortcomings, a film-formation-type anti-fungal composition consisting of halopropargylaryl ether, a cellulose derivative and a solvent of a low boiling point was proposed (JPN KOKOKU 55-49570). Generally speaking, however, the coating film formed by a cellulose derivative is coarse and, therefore, gives a bad feeling on an applied part unless softening agents are added. Further, the film is apt to come off easily. Therefore, the addition of a softening agent or the like was suggested to solve these shortcomings in the said patent publication. However, it is not desirable to use such softening agents, because those are irritative.

SUMMARY OF THE INVENTION

The present invention provides pharmaceutical preparations for the treatment of tinea pedis, containing as basic components about 0.1% to about 2.5% of croconazole hydrochloride and about 1%-15% of an ethyl acrylate-methyl methacrylate copolymer in an aqueous alcohol, and if necessary, about 0.1%-2.5% of a thickening agent and/or a plasticizer.

BRIEF DESCRIPTION OF THE DRAWING

The ordinate shows CCZ amount in the skin, while the abscissa shows time. The remaining amount of CCZ in the skin are shown by the marks "●" for the control and "○" for the Example 1 preparation.

DESCRIPTION OF THE PREFERRED EMBODIMENT

Problem to be Solved

In view of the above points, the present inventors tried to provide sustained release preparations of CCZ for tinea pedis which would form a soft and strong coating film on the affected parts without the use of any extra additive such as a softening agent; and thus completed the present invention. In this specification, the percentages of materials used indicate the percentages by weight (w/w%) of the materials to the total weight of the whole preparation.

Means to Solve the Problem

This invention can be achieved by dissolving about 0.1%—about 2.5% of CCZ and about 1%—about 15% of a copolymer of ethyl acrylate and methyl methacrylate (hereinafter abbreviated as EA-MMA) in an aqueous alcohol. If necessary, about 0.1%—about 2.5% of a thickening agent and/or a plasticizer may be further added. Eudragit ®E30D may be a good representative for EA-MMA. The aqueous alcohol used in this invention means a mixture of a lower alkanol and purified water. Lower alkanol includes, for example, ethanol, propanol, isopropanol, and the like. Aqueous alcohols whose alcohol content is between about 55% and 75% are preferably employed.

As thickening agents, such cellulose derivatives as ethyl cellulose (EC), hydroxypropyl cellulose (HPC) and hydroxypropylmethyl cellulose (HPMC) are preferably used; and as plasticizers, propylene glycol (PG), polyethylene glycol (PEG), etc., are preferably used.

The tinea pedis preparations of this invention enhance the transdermal absorbability of CCZ and make drug effectiveness last for a long time. So, it can be expected that once a day application of the preparation is enough to attain good efficacy.

This invention is explained in more detail in the following Examples and Experiments, which are not intended to limit the scope of the invention.

EXAMPLE 1

To 28.2 g of purified water were gradually added 4.0 g of EA-MMA and 1.0 g of EC, while being stirred in a closed vessel equipped with a stirrer, to give a uniform dispersion.

To said dispersion was added 65.8 g of isopropanol, and the mixture was stirred until the solution became clear. In the clear solution thus obtained was dissolved 1.0 g of CCZ with stirring, whereby 100.0 g of a tinea pedis preparation was obtained.

EXAMPLES 2-5

According to substantially the same manner as in Example 1, tinea pedis preparations consisting of such components as shown in Table 1 were obtained. The numeral shown in the table indicates how much the component was used (% by weight).

TABLE 1

| | Example | | | |
|---|---|---|---|---|
| Components | 2 (%) | 3 (%) | 4 (%) | 5 (%) |
| CCZ | 1.0 | 1.0 | 1.0 | 1.0 |
| EA · MMA | 4.0 | 4.0 | 4.0 | 10.0 |
| EC | | 1.0 | | 2.0 |
| HPC | 1.0 | | | |
| PG | | | 1.0 | |
| Purified water | 28.2 | 28.2 | 28.2 | 26.1 |
| Ethanol | | 65.8 | | |
| Isopropanol | 65.8 | | 65.8 | 60.9 |

EXPERIMENT

The in vivo transdermal absorption study shown in the following experiments were carried out, basically according to the undermentioned method:

Test method

1. Male Wistar rats (9 weeks of age, n=5-8) anesthetised by urethane have their abdominal hair removed carefully with electric clippers and electric razor.

2. The rat is fixed on its back, and then an absorption chamber (application area: 10 cm²) is fixed on the surface of the hairless abdomen with an binder.
3. A pre-fixed dose of a test material (3 mg as CCZ per rat) is placed into the chamber.
4. After a certain period of time, the coating film formed on the skin in the chamber is peeled off with distilled water and collected into suitable vessel.
5. The chamber is removed and the application area of the skin is cut off.
6. The sample in Item 4 and the piece of the skin in Item 5 are employed for the CCZ content measurement by HPLC.

EXPERIMENT 1

Study for transdermal absorption of CCZ were carried out in some preparations having different kinds of high molecular substances for the coating film to determine the CCZ amount in the skin at 4 hours after the application. Numerals in the table represent the percentage of addition (% by weight).

Preparation

TABLE 2

| Component | A | B | C |
|---|---|---|---|
| CCZ | 1 | 1 | 1 |
| MA · EA | 5 | | |
| DMAEM · ME | | 5 | |
| EA · MMA | | | 5 |
| 70% isopropanol | 94 | 94 | 94 |

Remark

MA.EA: Copolymer of methacrylic acid and ethyl acrylate

DMAEM.ME: Copolymer of dimethylaminoethyl methacrylate and ester of methacrylic acid Result

TABLE 3

| Composition | CCZ Amount in the Skin (mcg/10 cm²) |
|---|---|
| A | 3.8 |
| B | 13.1 |
| C | 28.5 |
| Control* | 26.7 |

Remark

Control *: 1% Pilzcin ® Cream (made by Shionogi & Co., Ltd.)

The transdermal absorbability of CCZ varied greatly with the sorts of the high molecular substances used as base materials. As compared with the control preparation, i.e., Pilzcin ® Cream, the preparations A and B in which MA.EA and DMAEM.ME were used respectively showed lower transdermal absorbabilities of CCZ. On the other hand, the preparation C in which EM.MMA employed in this invention was used showed an equal or a higher transdermal absorbability than that in the control preparation.

EXPERIMENT 2

The preparation of Example 1 was compared with the control preparation (1% Pilzcin Cream: commercially available) as to how long the drug effectiveness would last.

The CCZ amount in the skin was measured at several points of time according to the aforementioned test method.

(Result)

A result is shown in the drawing. As compared with the control, the preparation of this invention suppressed the maximum concentration in the skin and, at the same time, prolonged the time to reach there: this is the typical aspect seen in every sustained release preparation. Furthermore, the preparation of this invention showed a remarkably high value in AUC (area under the curve), the fact of which demonstrates a high bioavailability of CCZ.

From those results, it is expected that the tinea pedis preparations of this invention will give excellent efficacy in the treatment with only a once a day application.

What is claimed is:

1. A pharmaceutical preparation for the treatment of tinea pedis, comprising about 0.1% to about 2.5% of croconazole hydrochloride and about 1%–15% of an ethyl acrylate-methyl methacrylate copolymer in a pharmaceutically acceptable aqueous alcohol.

2. A pharmaceutical preparation for the treatment of tinea pedis claimed in claim 1, further comprising about 0.1% to about 2.5% of a thickening agent.

3. A pharmaceutical preparation for the treatment of tinea pedis claimed in claim 1, wherein said aqueous alcohol is about 55% to about 75% ethanol or isopropanol.

4. A pharmaceutical preparation for the treatment of tinea pedis claimed in claim 2, wherein said thickening agent is ethyl cellulose, hydroxypropyl cellulose or hydroxypropylmethyl cellulose.

5. A pharmaceutical preparation for the treatment of tinea pedis claimed in claim 2, wherein said aqueous alcohol is about 55% to about 75% ethanol or isopropanol.

* * * * *